(12) United States Patent
Sukkau et al.

(10) Patent No.: US 12,213,773 B2
(45) Date of Patent: Feb. 4, 2025

(54) PHYSIOLOGICAL ACQUISITION SYSTEM FOR USE IN AN RF-SHIELDED ROOM

(71) Applicant: Siemens Healthcare GmbH, Erlangen (DE)

(72) Inventors: Johann Sukkau, Herzogenaurach (DE); Klaus Ludwig, Erlangen (DE); Michael Roas-Löffler, Erlangen (DE); Christopher Horn, Erlangen (DE); Vincenzo Castiglione, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 332 days.

(21) Appl. No.: 17/901,900

(22) Filed: Sep. 2, 2022

(65) Prior Publication Data

US 2023/0068520 A1    Mar. 2, 2023

(30) Foreign Application Priority Data

Sep. 2, 2021 (DE) .......................... 102021209665.4

(51) Int. Cl.
*A61B 5/055* (2006.01)
*G01R 33/421* (2006.01)

(52) U.S. Cl.
CPC .......... *A61B 5/055* (2013.01); *G01R 33/4215* (2013.01); *A61B 2562/18* (2013.01)

(58) Field of Classification Search
CPC .. A61B 6/00; A61B 5/00; A61B 5/055; A61B 2562/18; G01R 33/4215; G01R 33/28; G01R 33/422; G01R 33/5673
See application file for complete search history.

(56) References Cited

U.S. PATENT DOCUMENTS

| | | | |
|---|---|---|---|
| 2008/0027306 A1* | 1/2008 | Washburn | A61B 5/055 600/410 |
| 2015/0279189 A1* | 10/2015 | Keene | G01V 3/08 340/540 |
| 2016/0131788 A1* | 5/2016 | Kopp | G01P 13/00 324/228 |
| 2021/0103016 A1* | 4/2021 | Horton | G01R 33/288 |

OTHER PUBLICATIONS

Alternative Übertragungsmethode von zeitsynchronisierten Zeigermessgerät-Daten in der Magnetresonanztomographie (Alternative transmission method of time-synchronized pointer meter data in magnetic resonance tomography); 2021.

* cited by examiner

*Primary Examiner* — Patricia J Park
*Assistant Examiner* — Michael Yiming Fang
(74) *Attorney, Agent, or Firm* — Banner & Witcoff Ltd.

(57) ABSTRACT

The disclosure relates to a radio-based physiological acquisition system for an RF-shielded room comprising a peripheral acquisition unit with a peripheral transmitter, a peripheral control unit, and a door sensor unit. The door sensor unit is configured to determine an opening status of a door in an RF shield around the RF-shielded room. The peripheral acquisition unit is configured to switch off the peripheral transmitter depending on the opening status of the door, e.g. when the door is open.

14 Claims, 3 Drawing Sheets

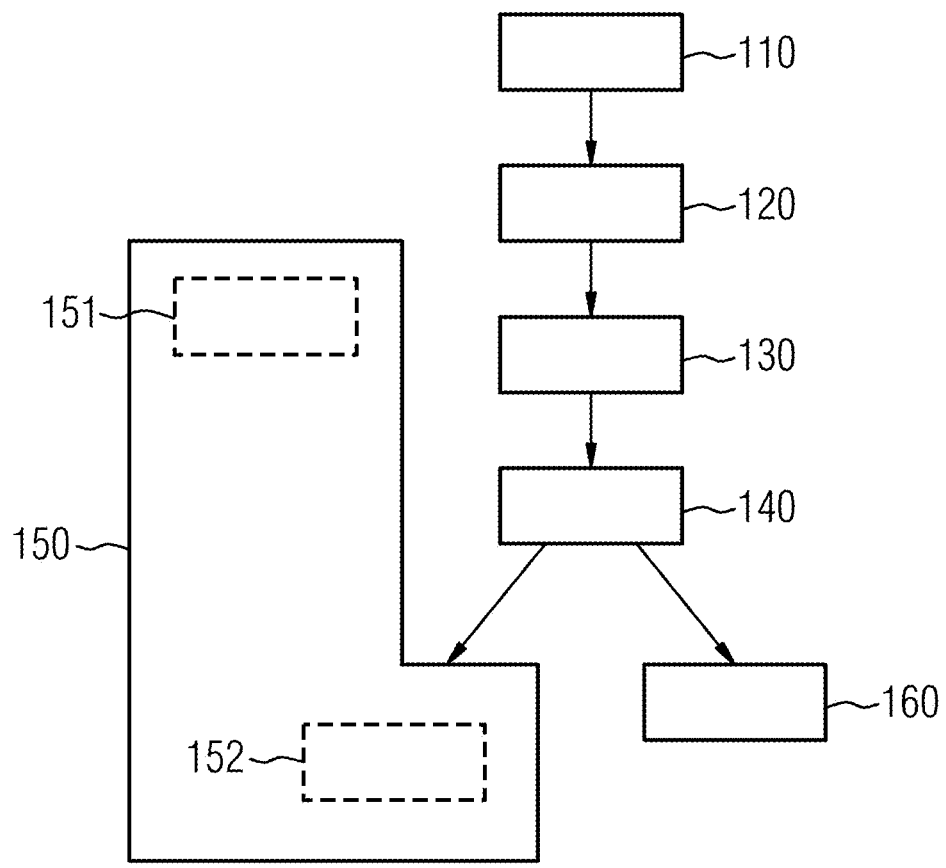

PHYSIOLOGICAL ACQUISITION SYSTEM FOR USE IN AN RF-SHIELDED ROOM

CROSS-REFERENCE TO RELATED APPLICATIONS

The present application claims the benefit of the filing date of Germany patent application no. DE 10 2021 209 665.4, filed on Sep. 2, 2021, the contents of which are incorporated herein by reference in their entirety.

TECHNICAL FIELD

The disclosure relates to a peripheral system designed to acquire physiological data from an examination object depending on the opening status of an RF shield enclosing the peripheral system, and to a magnetic resonance device and a magnetic resonance device system, each comprising such a peripheral system.

BACKGROUND

In a magnetic resonance device, the body to be examined of an examination object, in particular an examination object, is usually exposed to a relatively high main magnetic field of for example 1.5 or 3 or 7 tesla by means of a main magnet. In addition, a gradient coil unit is used to play out gradient pulses. Radiofrequency pulses, for example excitation pulses, are then transmitted via a radiofrequency antenna unit using suitable antenna facilities, causing the nuclear spins of particular atoms resonantly excited by these radiofrequency pulses to be tilted by a defined flip angle relative to the magnetic field lines of the main magnetic field. On relaxation of the nuclear spins, radiofrequency signals, known as magnetic resonance signals, are emitted which are received by means of suitable radiofrequency antennas and then undergo further processing. Finally, the desired image data can be reconstructed from the raw data acquired in this way.

Because of the radiofrequency signals transmitted and received during operation of a magnetic resonance device, a magnetic resonance device can typically only be operated in a room that provides shielding against external radiofrequency signals from the environment, and also prevents the radiofrequency signals generated during operation of the magnetic resonance device from propagating outside the room. Consequently, a magnetic resonance device is typically enclosed by a radiofrequency shield (RF shield) and accordingly disposed in an RF-shielded room. For example, the RF shield can be in the form of a Faraday cage. To enable the examination object to access the magnetic resonance device, the RF shield has a reversible opening, typically in the form of a door. This door is typically closed during operation of the magnetic resonance device, i.e. when the radiofrequency signals are being generated. During preparation for an examination, such a door is typically open to allow access by medical personnel.

A magnetic resonance device typically includes peripheral systems that enable the examination object to be monitored. A peripheral system may comprise a camera and/or an electrocardiography device (ECG device). A peripheral system is preferably designed to acquire time-resolved data from the examination object, said data not being magnetic resonance signals. A peripheral system is preferably designed to record a motion and/or a temperature of the examination object, and/or a respiration and/or a physiological effect, such as a heartbeat and/or an electrocardiogram. Such data acquired using a peripheral system can be termed peripheral data and/or physiological data. Peripheral data can also include a temperature of a magnetic resonance device, particularly of a component of a magnetic resonance device, and/or the temperature of the RF-shielded room. Peripheral data can also include audio data and/or video data, particularly for monitoring the examination object and/or for communicating with the examination object. Similarly, the peripheral data can also include audio data for entertaining the examination object, for example music, audio dramas, and/or videos. Peripheral systems may interact with a magnetic resonance device, for example as part of heartbeat- and/or motion-triggered acquisition of MR signals. Consequently, peripheral systems are typically linked to the magnetic resonance device, in particular to a control unit of the magnetic resonance device. In modern magnetic resonance devices, such a connection can be embodied as at least partially wireless, in particular radio-based. For this purpose, peripheral systems typically have a transmitter and a receiver that transmit and receive within the RF-shielded room.

SUMMARY

The object underlying the disclosure is to specify a peripheral system with wireless signal transmission that is embodied to be particularly low-emission. This object is achieved by the embodiments as described throughout the disclosure, including the claims.

The peripheral system according to the disclosure is configured to acquire peripheral data, e.g. physiological data, of an examination object, which examination object is disposed inside a room which at least partially encloses a magnetic resonance device and is RF-shielded. The peripheral system comprises a peripheral acquisition unit disposed inside the RF-shielded room. The peripheral acquisition unit comprises a peripheral transmitter, a peripheral receiver, and a sensor unit, which sensor unit is configured to acquire the peripheral data of the examination object.

The peripheral system comprises a peripheral control unit connected to (e.g. communicatively coupled to) the peripheral acquisition unit via a first wireless connection using a first transmission frequency. In an embodiment, the peripheral transmitter can be designed to transmit data, e.g. peripheral data, from the peripheral acquisition unit to the peripheral control unit on the first transmission frequency, wherein the transmission may be subject to conditions. In an embodiment, the peripheral receiver may be configured to receive data, e.g. control data, such as trigger signals and/or time data (such as a time stamp), from the peripheral control unit on the first transmission frequency, wherein the reception may be subject to conditions.

The peripheral system comprises a door sensor unit configured to determine an opening status of a door in an RF shield enclosing the RF-shielded room. The door sensor unit is linked (e.g. communicatively coupled) to the peripheral receiver via a second wireless connection using a second transmission frequency.

The peripheral acquisition unit is configured to turn off the peripheral transmitter depending on the opening status of the door, e.g. if the door is open.

The sensor unit is typically embodied to detect motion and/or a physiological effect. For example, the sensor unit may comprise an electrode designed for positioning on the chest of the examination object. The sensor unit may comprise a camera. The sensor unit may comprise an acceleration sensor.

The peripheral control unit may e.g. be disposed inside the RF-shielded room. The peripheral control unit may e.g. be wired to the magnetic resonance device, e.g. to the control unit thereof, and/or to a display unit. The peripheral control unit may also be disposed outside the RF-shielded room.

The first transmission frequency and/or the second transmission frequency may not include the resonance frequency of a hydrogen nuclear spin and/or sodium nuclear spin. The first transmission frequency and/or the second transmission frequency may be greater than the resonant frequency of a hydrogen nuclear spin at 3 tesla, in particular at 7 tesla. The first transmission frequency and the second transmission frequency may be different from one another.

The door sensor unit is typically configured to determine whether the RF shield is closed. The door sensor unit is configured to detect whether a door and/or reversible opening integrated in the RF shield is closed or open. For this purpose, the door sensor unit may comprise an optical sensor and/or a mechanical sensor and/or a magnetic sensor. The opening status may comprise information as to whether the door and/or reversible opening is closed or open. The door sensor unit may comprise a door sensor transmitting unit, which is configured to transmit the opening status on the second transmission frequency, e.g. to transmit the opening status to the peripheral receiver.

The peripheral acquisition unit may be configured to interrupt the first wireless connection and/or to terminate and/or temporarily suspend transmission of peripheral data from the peripheral transmitter to the peripheral control unit depending on the opening status, e.g. if the door is open. For instance, the peripheral acquisition unit may be configured to terminate and/or pause transmission of data from the peripheral control unit to the peripheral receiver by way of the first wireless connection.

Notwithstanding the wireless connection to the peripheral control unit and/or the magnetic resonance device, the peripheral system according to the disclosure operates in a particularly low-emission manner. In a completely RF-shielded room, e.g. with the RF shield closed and thus with the door closed, the peripheral system, and e.g. the wireless transmission of the acquired signals, is subject to no and/or a negligible interaction with the outside of the RF-shielded room. For instance, the RF shield attenuates the first wireless connection, i.e. the first transmission frequency, outside the RF-shielded room when the door is closed such that the first transmission frequency can no longer be measured there. It has been recognized that the acquisition of MR signals by the magnetic resonance device takes place with the door closed. The peripheral system is typically used simultaneously with the magnetic resonance device with the door closed. It has been recognized that a first wireless connection with the door closed is sufficient for stable operation of the peripheral system. Similarly, the operation of the peripheral system is typically not impaired if the first wireless connection, e.g. data transmission between the peripheral control unit and the peripheral acquisition unit, is interrupted when the door is open.

Accordingly, the peripheral system according to the disclosure is configured to maintain the first wireless connection only within a closed RF shield and to interrupt the first wireless connection as soon as the RF shield is not completely closed, for example in the form of an opened door. This reduces the radio emission from the peripheral system. For instance, this obviates the need for separate certification of the peripheral system with respect to compliance of the wireless connection, e.g. with respect to the first wireless connection and country-specific applicable radio regulations. This reduces the cost of such a peripheral system.

One embodiment of the peripheral system provides that the peripheral acquisition unit is configured to switch on the peripheral transmitter depending on the opening status of the door, e.g. when the door is closed. To be able to operate, the peripheral system typically requires a stable connection between the peripheral acquisition unit and the peripheral control unit, this being provided by means of a first wireless connection. This first wireless connection may be maintained by the peripheral acquisition unit depending on the opening status, e.g. interrupted when the door is open and/or activated when the door is closed. According to this embodiment, the peripheral transmitter may be controlled by the peripheral acquisition unit depending on the opening status, e.g. stopped when the door is open and/or activated when the door is closed. This embodiment enables particularly robust and automated functionality of the peripheral system, characterized e.g. by rapid availability of the peripheral system when the door is closed.

One embodiment of the peripheral system provides that the peripheral receiver is switched on regardless of the opening status of the door. As the peripheral receiver is not configured for radio emission, but is instead designed purely as a receiving unit, the peripheral receiver is not subject to any regulations with respect to radio emissions. Continuous functionality of the peripheral receiver enables a continuous second wireless connection with the door sensor unit, thereby ensuring rapid availability of the peripheral system when the door is closed.

According to one embodiment of the peripheral system, the peripheral transmitter is configured to transmit data only on the first transmission frequency. According to this embodiment, the peripheral transmitter can e.g. transmit peripheral data to the peripheral control unit using the first wireless connection. According to this embodiment, transmission of data on the second transmission frequency, if different from the first transmission frequency, is precluded, which also prevents bilateral communication with the door sensor unit. In addition to the software, a peripheral acquisition unit to be used for this peripheral system differs from conventional peripheral acquisition units with respect to the peripheral receiver, which is connected to (e.g. communicatively coupled to) the door sensor unit by a second wireless connection, i.e. differs only slightly therefrom. Retrofitting of existing peripheral systems can thus be realized in an inexpensive manner with an appropriate peripheral receiver and door sensor unit.

One embodiment of the peripheral system provides that the first transmission frequency is comprised by one of the following frequency ranges:
  a first frequency range comprising frequencies between 2350 MHz and 2550 MHz, e.g. between 2380 MHz and 2500 MHz, or e.g. between 2400 MHz and 2485 MHz;
  a second frequency range comprising frequencies between 5090 MHz and 5410 MHz, e.g. between 5110 MHz and 5390 MHz, or e.g. between 5150 MHz and 5350 MHz;
  a third frequency range comprising frequencies between 5400 MHz and 5800 MHz, e.g. between 5440 MHz and 5750 MHz, or e.g. between 5470 MHz and 5725 MHz.

The first transmission frequency can correspond to the Bluetooth frequency, typically 2.4 GHz. Consequently, corresponding transmitters and receivers for use as peripheral receivers and/or peripheral transmitters and/or within the peripheral control unit are commercially available and thus particularly inexpensive.

One embodiment of the peripheral system provides that the first transmission frequency correspond to the second transmission frequency. According to this embodiment, typically only one peripheral receiver is required, which is designed to receive data from the door sensor unit and data from the peripheral control unit, e.g. to form the first wireless connection and the second wireless connection, respectively. According to this embodiment, the first transmission frequency may correspond e.g. to the second transmission frequency. The first transmission frequency and the second transmission frequency may correspond to the Bluetooth frequency. The peripheral system according to this embodiment is particularly compact and cost-effective.

One embodiment of the peripheral system provides that the peripheral receiver comprises a first receiver unit configured to receive data transmitted from the peripheral control unit to the peripheral acquisition unit on the first transmission frequency, and a second receiver unit configured to receive data transmitted from the door sensor unit to the peripheral acquisition unit on the second transmission frequency. This embodiment is particularly advantageous if the first transmission frequency is different from the second transmission frequency. According to this embodiment, the first wireless connection and the second wireless connection are particularly reliable.

According to one embodiment of the peripheral system, the second transmission frequency is comprised of a fourth frequency range comprising frequencies between 420 MHz and 450 MHz, e.g. between 430 MHz and 440 MHz, or e.g. between 433 MHz and 435 MHz. This fourth frequency range encompasses "radio applications for short-range wireless devices (SRD),", which is particularly suitable for data exchange between the door sensor unit and the peripheral receiver. The door sensor unit may have e.g. a suitable transmitting unit, e.g. a door sensor transmitting unit for generating signals at the second transmission frequency. Such transmitting units are typically commercially available and do not require any particular certification in accordance with country-specific radio regulations. The same typically applies to the corresponding peripheral receiver because it has no transmission capability. Accordingly, this embodiment of the peripheral system is easily certifiable and/or does not require certification. According to this embodiment, the second transmission frequency may be different from the first transmission frequency, which corresponds for example to the Bluetooth frequency, typically 2.4 GHz. According to this embodiment, the peripheral receiver may e.g. comprise a first receiver unit and a second receiver unit.

The peripheral system may be embodied such that the second transmission frequency is comprised by one of the following frequency ranges:
- a fourth frequency range comprising frequencies between 430 MHz and 440 MHz;
- a fifth frequency range comprising frequencies between 40.6 MHz and 40.8 MHz;
- a sixth frequency range comprising frequencies between 2.4 GHz and 2.5 GHz;
- a seventh frequency range comprising frequencies between 5.7 MHz and 5.9 MHz.

One embodiment of the peripheral system provides that the peripheral acquisition unit is configured to acquire peripheral data of an examination object depending on the opening status of the door, e.g. only when the door is closed. The acquisition of peripheral data can take place e.g. before the start of MR signal acquisition, e.g. as part of a learning phase during which initialization and/or analysis of the peripheral data, for example of an ECG signal, can take place individually for the examination object. The peripheral data acquired in the learning phase enables a more robust analysis of peripheral data acquired simultaneously with the acquisition of MR signals.

The door sensor unit may be configured to transmit information regarding the closing of the door to the peripheral receiver, e.g. to the peripheral acquisition unit via the second wireless connection, for example as a trigger signal. The peripheral acquisition unit may be configured to evaluate this trigger signal indicating closing of the door as a start criterion for acquiring peripheral data. For instance, the peripheral acquisition unit and/or the peripheral control unit may start acquiring peripheral data. This embodiment ensures that peripheral data is not acquired and transmitted using the first wireless connection when the door is open.

One embodiment of the peripheral system provides that the peripheral system additionally comprises an optical receiver and an optical transmitter, wherein the optical transmitter is comprised by the peripheral acquisition unit, the optical receiver is wired to the peripheral control unit, and the peripheral acquisition unit is configured to perform data transfer from the optical transmitter to the optical receiver by means of an optical link depending on the opening status of the door, e.g. when the door is open and/or when the peripheral transmitter is switched off. The optical connection may be based on infrared light. The optical receiver is e.g. disposed inside the detector unit and/or at the longitudinal end of a hollow cylindrical detector unit. The connecting line between the optical receiver and the optical transmitter may be unobstructed. The optical receiver may be designed to receive peripheral data from the optical transmitter and to forward it to the peripheral control unit.

This embodiment enables two independent connections between the peripheral acquisition unit and the peripheral control unit, e.g. by way of the first wireless connection and the optical connection. The optical link is typically free of radio emission and enables data exchange between the peripheral acquisition unit and the peripheral control unit when the RF shield is open, e.g. when the door is open. This is especially advantageous as part of a learning phase prior to the start of MR signal acquisition. For instance, the period of time until medical personnel leave the RF-shielded room and close the door after completing the preparation can be used for the learning phase. This can reduce the duration of a magnetic resonance examination. The peripheral system can therefore be initialized individually for the examination object without radio emission even with the doors open. The peripheral data to be obtained simultaneously with the MR signals can be acquired and processed in the usual quality after the door is closed. This embodiment enables particularly time-efficient use of the peripheral system while at the same time ensuring suppression of radio emission irrespective of the opening status of the door.

Embodiments also include a magnetic resonance device comprising a peripheral system according to the disclosure and a detector unit configured to receive MR signals from an examination object, which detector unit is disposed inside an RF-shielded room. The RF-shielded room and/or the RF shield enclosing the RF-shielded room can also be comprised by the magnetic resonance device. The magnetic resonance device may additionally comprise a control unit configured to process MR signals and to control the detector unit, wherein the control unit is disposed outside the RF-shielded room and wired to the detector unit and the peripheral control unit.

The disclosure also relates to a magnetic resonance device system comprising at least two magnetic resonance devices, each comprising a detector unit. At least one magnetic resonance device of the at least two magnetic resonance devices comprises a peripheral system according to the disclosure. The magnetic resonance device system also comprises at least two RF-shielded rooms, wherein the at least two magnetic resonance devices are disposed separately from each other each in a RF-shielded room of the at least two RF-shielded rooms. Consequently, in each case one magnetic resonance device of the at least two magnetic resonance devices is disposed in a respective RF-shielded room. For instance, the peripheral system according to the disclosure ensures that when a door of an RF-shielded room is open, transmission of the peripheral data is disabled, thereby ensuring that a peripheral control unit associated with the other magnetic resonance device does not receive the peripheral data. As a result, interference can be prevented.

The peripheral system according to the disclosure is typically a radio-based physiological acquisition system for an RF-shielded room comprising a peripheral acquisition unit having a peripheral transmitter, a peripheral control unit, and a door sensor unit, which door sensor unit is configured to determine the opening status of a door in an RF shield enclosing the RF-shielded room, wherein the peripheral acquisition unit is configured to switch off the peripheral transmitter depending on the opening status of the door, e.g. when the door is open.

Embodiments additionally include a method for examining an examination object using a magnetic resonance device according to the disclosure, comprising the following method steps:
  positioning the examination object in the RF-shielded room;
  disposing the peripheral acquisition unit on the examination object;
  positioning the examination object in a patient receiving area enclosed by the detector unit;
  closing the door of the RF-shielded room;
  acquiring peripheral data of the examination object;
  acquiring MR signals of the examination object.

An optimal position for disposing the peripheral acquisition unit on the examination object can be marked and/or assisted by means of optical identification, for example by means of LEDs.

According to one embodiment of the method, the acquisition of the peripheral data comprises acquiring training data and acquiring examination data, wherein the training data is acquired at least partially before the door is closed and after the peripheral acquisition unit has been placed on the examination object.

According to this embodiment, the examination data is acquired after the door is closed and the training data is at least partially used for initializing the examination data. The magnetic resonance device used for this embodiment typically comprises a peripheral system additionally comprising the optical receiver and the optical transmitter. The training data is typically used as part of a learning phase and/or enables the examination data to be initialized individually for the examination object.

Embodiments of the magnetic resonance device according to the disclosure, the magnetic resonance device system according to the disclosure, and the method according to the disclosure are analogous to embodiments of the peripheral system according to the disclosure. The magnetic resonance device may have further units that are necessary and/or advantageous for the integration of the peripheral system.

The advantages of the magnetic resonance device according to the disclosure and of the magnetic resonance device system according to the disclosure essentially correspond to the advantages of the peripheral system according to the disclosure, as set forth in detail above. Features, advantages, or alternative embodiments mentioned herein can likewise be applied to the other claimed objects, and vice versa.

BRIEF DESCRIPTION OF THE DRAWINGS/FIGURES

Further advantages, features and details of the disclosure will emerge from the exemplary embodiments described below and on the basis of the drawings in which:

FIG. 5 shows a flow chart of an embodiment of a method according to the disclosure.

DETAILED DESCRIPTION

Figure 1:
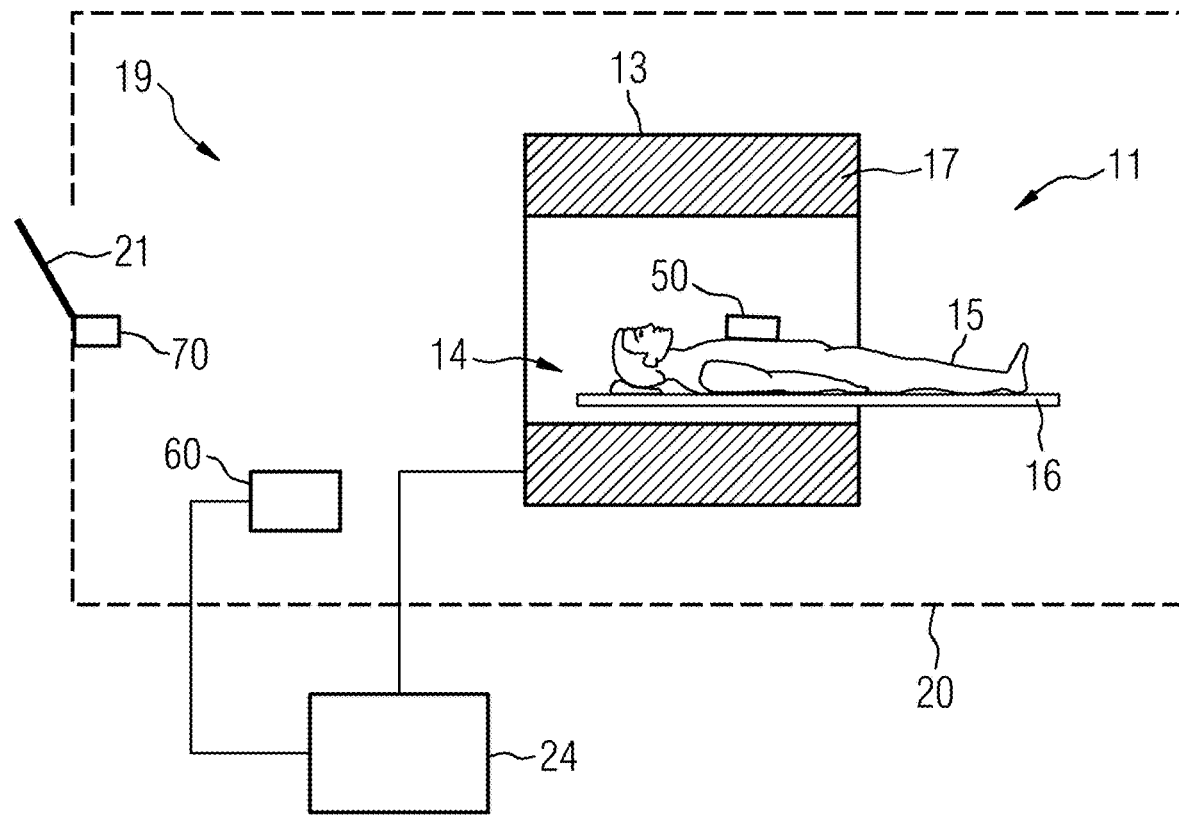
FIG. 1 shows a schematic illustration of a first embodiment of a magnetic resonance device according to the disclosure.

FIG. 1 shows a schematic illustration of a magnetic resonance device 11 for carrying out a method according to the disclosure. The magnetic resonance device 11 comprises a detector unit 13, configured to generate and detect MR signals emanating from an examination object 15. In addition, the magnetic resonance device 11 has a cylindrical patient receiving area 14 for accommodating an examination object 15, wherein the patient receiving area 14 is cylindrically enclosed in a circumferential direction by the detector unit 13. The examination object 15 can be moved into the patient receiving area 14 by means of a patient positioning apparatus 16 of the magnetic resonance device 11. For controlling the detector unit 13, typically comprising an acquisition unit 17 comprising a main magnet, a gradient coil unit, and a radiofrequency antenna unit, the magnetic resonance device 11 has a control unit 24. The control unit 24 centrally controls the magnetic resonance device 11, for example the execution of MR control sequences.

At least the detector unit 13 and/or the examination area are disposed within an RF-shielded room 19. The RF-shielded room 19 is enclosed by an RF shield 20, wherein the RF shield 20 comprises a reversibly closable opening, e.g. a door 21. The control unit 24 may be disposed outside the RF-shielded room 19. The magnetic resonance device 11 according to the disclosure comprises a peripheral system according to the disclosure, which is disposed at least partially inside the RF-shielded room 19. The peripheral acquisition unit 50 comprised by the peripheral system may be disposed inside the patient receiving area 14. The peripheral acquisition unit 50 may be disposed on the surface of the examination object 15 and/or disposed at any suitable distance e.g. of no more than 15 cm, no more than 10 cm, no more than 5 cm, etc. from the surface of the examination object 15. According to this embodiment, the peripheral control unit 60 is disposed inside the RF-shielded room 19. The peripheral system comprises a door sensor unit 70, which is typically located at any suitable distance e.g. less than 40 cm, less than 25 cm, less than 10 cm, etc. from the RF shield 20 and/or door 21. The door sensor unit 70 may be disposed inside or outside the RF-shielded room 19. The door sensor unit 70 may be configured as part of the RF shield 20 and/or part of the door 21. The peripheral control unit 60 may be wired to the control unit 24.

The magnetic resonance device 11 as illustrated in FIG. 1 may include other components that magnetic resonance devices 11 typically implement or otherwise utilize. Moreover, the general mode of operation of a magnetic resonance device 11 is known to persons skilled in the art, so that a detailed description of the additional components can be dispensed with.

Figure 2:
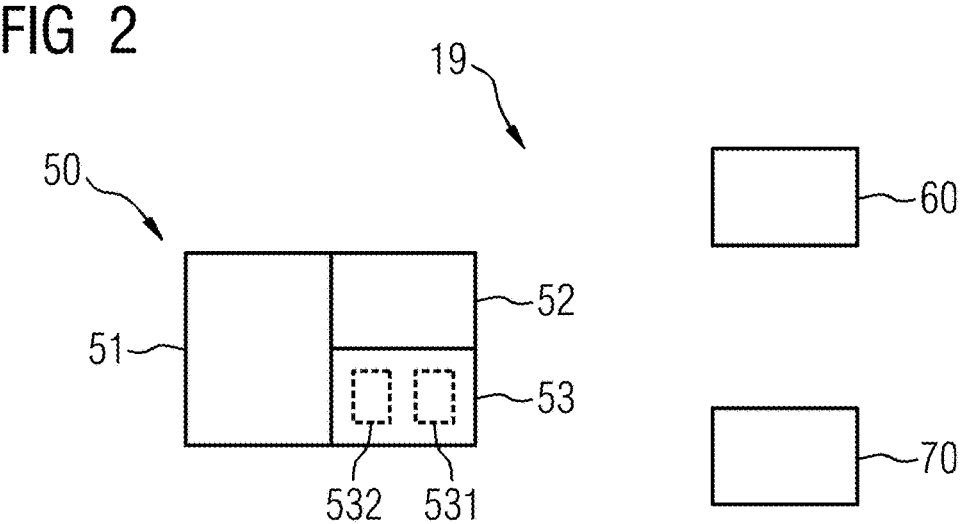
FIG. 2 shows a schematic illustration of a first embodiment of a peripheral system according to the disclosure.

FIG. 2 shows a schematic illustration of a first embodiment of a peripheral system according to the disclosure. The peripheral system comprises a peripheral acquisition unit 50 that is disposed inside an RF-shielded room 19. The peripheral acquisition unit 50 comprises a peripheral transmitter 52, a peripheral receiver 53, and a sensor unit 51, which sensor unit 51 is configured to acquire peripheral data of an examination object 15. The peripheral system according to the disclosure further comprises a peripheral control unit 60, which is linked (e.g. communicatively coupled) to the peripheral acquisition unit 50 via a first wireless connection using a first transmission frequency. The peripheral system according to the disclosure additionally comprises a door sensor unit 70 configured to determine an opening status of a door 21 disposed in an RF shield 20 around the RF-shielded room 19. The door sensor unit 70 is connected to (e.g. communicatively coupled to) the peripheral receiver 53 via a second wireless connection using a second transmission frequency. The peripheral acquisition unit 50 is configured to turn off the peripheral transmitter 52 depending on the opening status of the door 21, e.g. when the door 21 is open. The peripheral acquisition unit 50 may be configured to obtain peripheral data of an examination object 15 depending on the opening status of the door 21, e.g. only when the door 21 is closed.

The peripheral transmitter 52 is e.g. configured to transmit data only on the first transmission frequency. The peripheral acquisition unit 50 is e.g. configured to switch on the peripheral transmitter 52 depending on the opening status of the door 21, e.g. when the door 21 is closed. The peripheral receiver 53 can be switched on irrespective of the opening status of the door 21.

The peripheral receiver 53 can optionally comprise a first receiver unit 531, said first receiver unit 531 being configured to receive data that is transmitted from the peripheral control unit 60 to the peripheral acquisition unit 50 on the first transmission frequency. The peripheral receiver 53 can optionally comprise a second receiver unit 532, said second receiver unit 532 being designed to receive data that is transmitted from the door sensor unit 70 to the peripheral acquisition unit 50 on the second transmission frequency.

Figure 3:
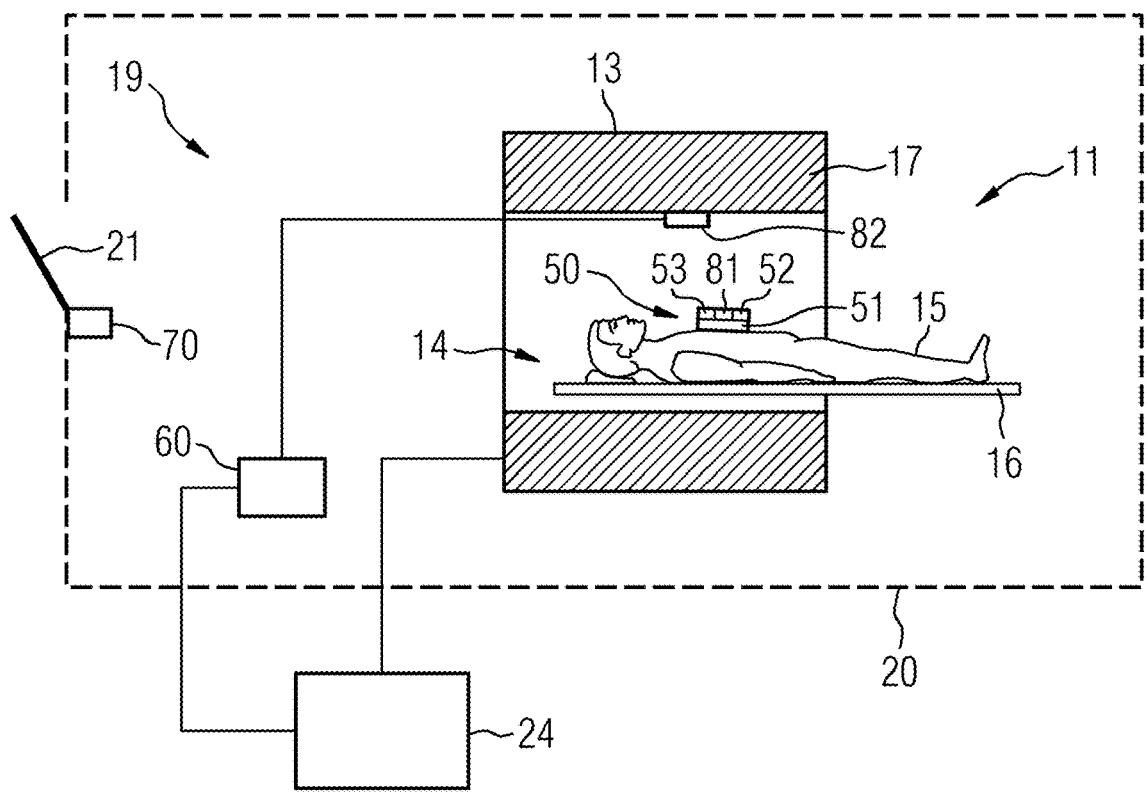
FIG. 3 shows a schematic illustration of a second embodiment of a peripheral system according to the disclosure.

FIG. 3 shows a schematic illustration of a magnetic resonance device 11 comprising a second embodiment of a peripheral system. In contrast to the first embodiment of the inventive magnetic resonance device 11 shown in FIG. 1, the peripheral system as shown in FIG. 3 additionally comprises an optical receiver 82 and an optical transmitter 81. The optical transmitter 81 is comprised by the peripheral acquisition unit 50. The optical receiver 82 is wired to the peripheral control unit 60, and the peripheral acquisition unit 50 is designed for data transfer from the optical transmitter 81 to the optical receiver 82 by way of an optical connection depending on the opening status of the door 21.

Figure 4:
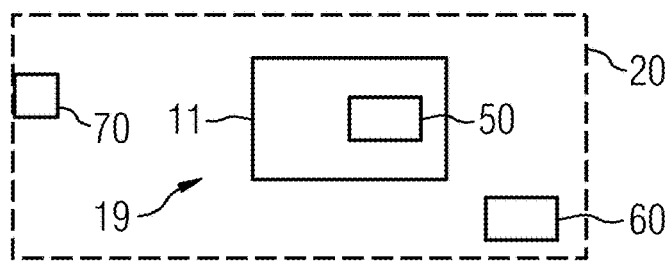
FIG. 4 shows a schematic illustration of a magnetic resonance device system according to the disclosure.
Figure 4:
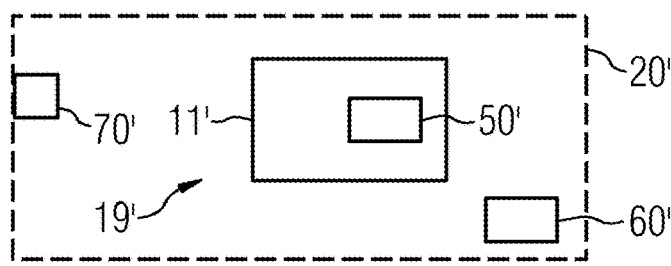

FIG. 4 shows a schematic illustration of a magnetic resonance device system according to the disclosure. The magnetic resonance device system comprises two magnetic resonance devices 11, 11' each comprising a detector unit 13 and two RF-shielded rooms 19, 19', wherein the at least two magnetic resonance devices 11, 11' are disposed separately from one another in the at least two RF-shielded rooms 19, 19'.

FIG. 5 shows a flow chart of an embodiment of a method according to the disclosure for examining an examination object 15 using a magnetic resonance device 11, 11' according to the disclosure.

Block 110 of the method makes provision for positioning the examination object 15 in the RF-shielded room 19.

Block 120 comprises disposing the peripheral acquisition unit 50 on the examination object 15.

Block 130 comprises positioning the examination object 15 in a patient receiving area 14 enclosed by the detector unit 13.

Block 140 comprises closing the door 21 of the RF-shielded room 19.

Block 150 makes provision for acquiring peripheral data of the examination object 15.

Block 160 comprises acquiring MR signals of the examination object 15.

Blocks 110, 120, 130, 140, 150, 160 can be performed in the order as shown or in a different order. For example, the blocks 150 and 160 may be executed at least partly simultaneously. Likewise, the blocks 130 and 140 may be executed at least partly simultaneously. Also, the execution of block 150 may at least partially overlap with the execution of the blocks 130 and/or 140.

Optionally, block 150 may comprise the acquisition of training data with the block 151, which is executed at least partially before the door 21 is closed, i.e. before the block 140, and after the peripheral acquisition unit 50 has been disposed on the examination object 15, i.e. after the block 120. Additionally, the block 150 may comprise acquiring examination data with the block 152, wherein the block 152 is executed after the door 21 is closed, i.e. after the block 140.

Although the disclosure has been illustrated and described in detail by the preferred exemplary embodiments, the disclosure is not limited by the disclosed examples and other variations will be apparent to persons skilled in the art without departing from the scope of protection sought for the disclosure The various components described herein may be referred to as "units." Such components may be implemented via any suitable combination of hardware and/or software components as applicable and/or known to achieve their intended respective functionality. This may include mechanical and/or electrical components, processors, processing circuitry, or other suitable hardware components configured to execute instructions or computer programs that are stored on a suitable computer readable medium. Regardless of the particular implementation, such "units," as applicable and relevant, may alternatively be referred to herein as "circuitry," "processors," or "processing circuitry."

What is claimed is:

1. A peripheral system for acquiring physiological data associated with an examination object that is disposed inside a radio frequency (RF)-shielded room that at least partially encloses a magnetic resonance device, the system comprising:

peripheral acquisition circuitry disposed inside the RF-shielded room, the peripheral acquisition circuitry comprising a peripheral data sensor configured to acquire the physiological data, a peripheral transmitter configured to transmit the physiological data, and a peripheral receiver;

peripheral control circuitry communicatively coupled to the peripheral acquisition circuitry via a first wireless connection using a first frequency; and a door sensor configured to identify an opening status of a door associated with an RF shield of the RF-shielded room, the door sensor being communicatively coupled to the peripheral receiver via a second wireless connection using a second frequency, wherein the peripheral acquisition circuitry is configured to switch off the peripheral transmitter when the identified opening status of the door indicates that the door is open.

2. The peripheral system as claimed in claim 1, wherein the peripheral acquisition circuitry is configured to switch on the peripheral transmitter when the identified opening status of the door indicates that the door is closed.

3. The peripheral system as claimed in claim 1, wherein the peripheral receiver is switched on independently of the identified opening status of the door.

4. The peripheral system as claimed in claim 1, wherein the peripheral receiver comprises:
   a first receiver configured to receive data transmitted by the peripheral control circuitry to the peripheral acquisition circuitry on the first frequency; and
   a second receiver configured to receive data transmitted by the door sensor to the peripheral acquisition circuitry on the second frequency.

5. The peripheral system as claimed in claim 1, wherein the peripheral transmitter is configured to transmit data only on the first frequency.

6. The peripheral system as claimed in claim 1, wherein the first frequency and the second frequency are the same frequency.

7. The peripheral system as claimed in claim 1, wherein the first frequency comprises one of (i) a frequency range comprising frequencies between 2350 MHz and 2550 MHz, (ii) a frequency range comprising frequencies between 5090 MHz and 5410 MHz, or (iii) a frequency range comprising frequencies between 5400 MHz and 5800 MHz.

8. The peripheral system as claimed in claim 1, wherein the second frequency comprises one of (i) a frequency range comprising frequencies between 430 MHz and 440 MHz, (ii) a frequency range comprising frequencies between 40.6 MHz and 40.8 MHz, (iii) a frequency range comprising frequencies between 2.4 GHz and 2.5 GHz, or (iv) a frequency range comprising frequencies between 5.7 MHz and 5.9 MHz.

9. The peripheral system as claimed in claim 1, wherein the peripheral acquisition circuitry is configured to acquire the physiological data of the examination object when the identified opening status of the door indicates that the door is closed.

10. The peripheral system as claimed claim 1, further comprising:
    an optical receiver,
    wherein the peripheral acquisition circuitry further comprises an optical transmitter,
    wherein the optical receiver is coupled to the peripheral control circuitry, and
    wherein the peripheral acquisition circuitry is configured to transfer data from the optical transmitter to the optical receiver via an optical connection when the identified opening status of the door indicates that the door is open and/or when the peripheral transmitter is switched off.

11. A magnetic resonance (MR) device, comprising:
    a peripheral system configured to acquire physiological data associated with an examination object that is disposed inside a radio frequency (RF)-shielded room that at least partially encloses the magnetic resonance device, the peripheral system comprising:
        peripheral acquisition circuitry disposed inside the RF-shielded room, the peripheral acquisition circuitry comprising a peripheral data sensor configured to acquire the physiological data, a peripheral transmitter configured to transmit the physiological data, and a peripheral receiver;
        peripheral control circuitry communicatively coupled to the peripheral acquisition circuitry via a first wireless connection using a first frequency; and
        a door sensor configured to identify an opening status of a door associated with an RF shield of the RF-shielded room, the door sensor being communicatively coupled to the peripheral receiver via a second wireless connection using a second frequency,
        wherein the peripheral acquisition circuitry is configured to switch off the peripheral transmitter when the identified opening status of the door indicates that the door is open; and
    a detector disposed inside the RF-shielded room and configured to receive MR signals from the examination object.

12. The MR device of claim 11, wherein the MR device is from among a plurality of MR devices, each one of the plurality of MR devices (i) comprising a detector, and (ii) being disposed separately from one another within respective RF-shielded rooms.

13. A method for examining an examination object using a magnetic resonance (MR) device, comprising:
    positioning the examination object in a radio frequency (RF)-shielded room;
    disposing peripheral acquisition circuitry on the examination object, the peripheral acquisition circuitry comprising a peripheral data sensor configured to acquire the physiological data, a peripheral transmitter configured to transmit the physiological data, and a peripheral receiver, the peripheral acquisition circuitry being communicatively coupled to peripheral control circuitry via a first wireless connection using a first frequency;
    positioning the examination object in a patient receiving area at least partially enclosed by a detector;
    closing the door of the RF-shielded room;
    identifying, via a door sensor that is communicatively coupled to the peripheral receiver via a second wireless connection using a second frequency, an opening status of the door;
    acquiring physiological data of the examination object; and
    acquiring MR signals of the examination object,
    wherein the peripheral acquisition circuitry is configured to switch off the peripheral transmitter when the identified opening status of the door indicates that the door is open.

14. The method as claimed in claim 13, wherein the act of acquiring the physiological data of the examination object comprises:
    acquiring training data at least partially before the door is closed and after the peripheral acquisition circuitry has been disposed on the examination object; and acquiring examination data after the door has been closed,
wherein the training data is used at least partially for
   initializing the examination data.

\* \* \* \* \*